(12) United States Patent
Van Neerven

(10) Patent No.: US 7,759,133 B2
(45) Date of Patent: Jul. 20, 2010

(54) METHOD OF DETECTING AND/OR QUANTIFYING A SPECIFIC IGE ANTIBODY IN A LIQUID SAMPLE

(75) Inventor: Joost Van Neerven, Almere (NL)

(73) Assignee: ALK-Abello A/S, Almere (NL)

( * ) Notice: Subject to any disclaimer, the term of this patent is extended or adjusted under 35 U.S.C. 154(b) by 0 days.

(21) Appl. No.: 09/467,901

(22) Filed: Dec. 21, 1999

(65) Prior Publication Data

US 2001/0055778 A1    Dec. 27, 2001

Related U.S. Application Data

(60) Provisional application No. 60/113,536, filed on Dec. 22, 1998.

(30) Foreign Application Priority Data

Dec. 22, 1998    (DK) .......................... PA 1998 01709

(51) Int. Cl.
*G01N 33/566* (2006.01)
*C12Q 1/00* (2006.01)

(52) U.S. Cl. ...................... 436/501; 436/513; 436/518; 436/526; 436/538; 436/546; 436/548; 436/164; 436/166; 436/172; 436/800; 436/805; 436/806; 435/4; 435/7.1; 435/7.2; 435/7.5; 435/7.92; 435/7.93; 435/7.94; 435/7.95

(58) Field of Classification Search ............... 436/501, 436/513, 518, 526, 538, 546, 548, 164, 166, 436/172, 800, 805, 806; 435/4, 7.4, 7.2, 435/7.5, 7.92–7.95

See application file for complete search history.

(56) References Cited

U.S. PATENT DOCUMENTS

| | | | | |
|---|---|---|---|---|
| 4,859,612 A | * | 8/1989 | Cole et al. | 436/523 |
| 5,415,994 A | | 5/1995 | Imrich et al. | 435/5 |
| 5,512,659 A | * | 4/1996 | Ullman et al. | 530/391.1 |
| 5,693,758 A | | 12/1997 | Gould et al. | |
| 5,766,943 A | | 6/1998 | Lynch et al. | |
| 5,945,294 A | * | 8/1999 | Frank et al. | 435/7.9 |
| 5,965,605 A | | 10/1999 | Cheng et al. | |

(Continued)

FOREIGN PATENT DOCUMENTS

EP    0 499 112 A1    2/1992

(Continued)

OTHER PUBLICATIONS

Nissim et al., Fine Specificity Of The IgE Interaction With The Low And High Affinity Fc Receptor, The Journal of Immunology, vol. 150, 1365-1374 1993.

(Continued)

*Primary Examiner*—Jacob Cheu
*Assistant Examiner*—Pensee T Do
(74) *Attorney, Agent, or Firm*—Finnegan, Henderson, Farabow, Garrett & Dunner, L.L.P.

(57) ABSTRACT

Methods of detecting and/or quantifying an IgE antibody present in a liquid sample. The IgE antibody is specific to a ligand in the form of an antigen, an antibody, or a hapten. These methods can be used for monitoring and evaluating the immunological status of a subject.

22 Claims, 13 Drawing Sheets

U.S. PATENT DOCUMENTS

| | | | | |
|---|---|---|---|---|
| 5,994,511 | A | * | 11/1999 | Lowman et al. .......... 530/387.3 |
| 6,004,745 | A | * | 12/1999 | Arnold, Jr. et al. |
| 6,034,066 | A | * | 3/2000 | Johnson et al. ............... 514/18 |
| 6,037,453 | A | * | 3/2000 | Jardieu et al. ............ 530/387.3 |
| 6,060,326 | A | * | 5/2000 | Frank et al. ................. 436/513 |
| 6,066,718 | A | * | 5/2000 | Hardman et al. ............ 530/387 |
| 6,078,782 | A | * | 6/2000 | Leland et al. .................. 455/6 |
| 5,616,719 | A | * | 7/2000 | Davalian et al. ............ 546/334 |
| 6,087,188 | A | * | 7/2000 | Johansen et al. ............ 436/526 |
| 6,172,213 | B1 | * | 1/2001 | Lowman et al. ......... 536/23.53 |
| 6,379,909 | B1 | | 4/2002 | Ipsen et al. |
| 6,939,681 | B1 | | 9/2005 | Ipsen et al. |
| 2005/0239151 | A1 | | 10/2005 | Ipsen et al. |
| 2007/0224654 | A1 | | 9/2007 | Ipsen et al. |

FOREIGN PATENT DOCUMENTS

| | | |
|---|---|---|
| WO | WO 94/01775 | 1/1994 |
| WO | WO 94/11734 | 5/1994 |
| WO | WO 94/29696 | 12/1994 |
| WO | WO 97/24617 | 7/1997 |
| WO | WO 98/23964 | 6/1998 |
| WO | WO 98/27208 | 6/1998 |
| WO | WO 98/37099 | 8/1998 |
| WO | WO 98/45707 | 10/1998 |
| WO | WO 99/51988 | 10/1999 |

OTHER PUBLICATIONS

Stämpfli et al., Antigen-Specific Inhibition Of IgE Binding To The High-Affinity Receptor, The J. of Immunol., vol. 155, 2948-2954, 1995.

Meng, et al., Binding Of Cynomolgus Monkey IgE To A Humanized Anti-Human IgE Antibody And Human High Affinity IgE Receptor, Molecular Immunol., vol. 33, 635-642, 1996.

Guo et al., Autoantibody-Mediated Capture And Presentation Of Autoantigen To T Cells Via The Fcε Receptor By A Recombinant Human Autoantibody Fab Converted to IgE, J. Immunol. Methods, vol. 1995, 81-92, 1996.

Patent Abstracts of Japan, vol. 95, No. 6 Abstract of JP 70-72150, Mar. 17, 1995.

Derwent Accession No. 96-218218 Specific Measure of Immunoglobulin E Inducing Allergic Reation by Reacting Immunoglobulin E with Alpha Chain of High Affinity Receptor.

* cited by examiner

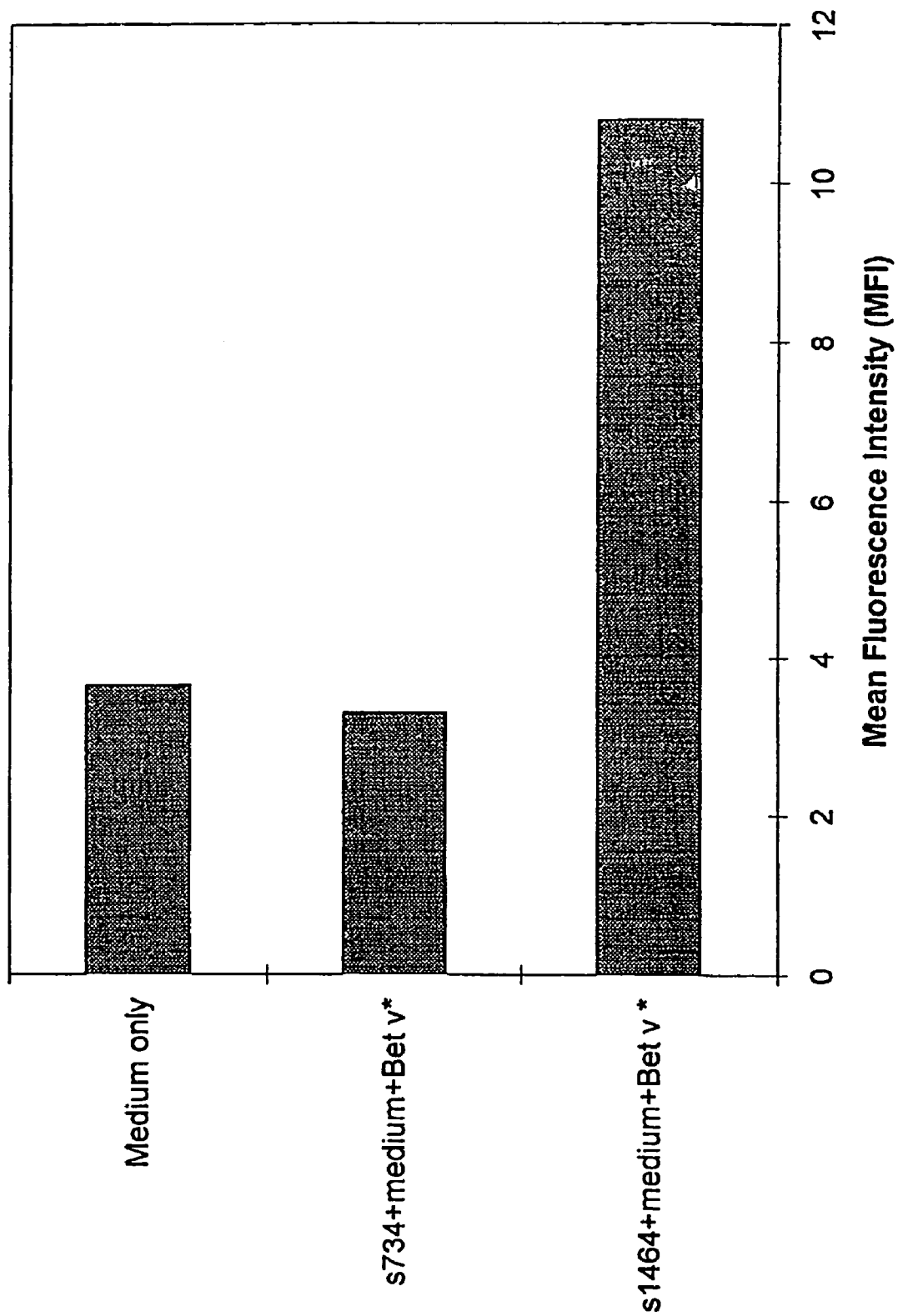

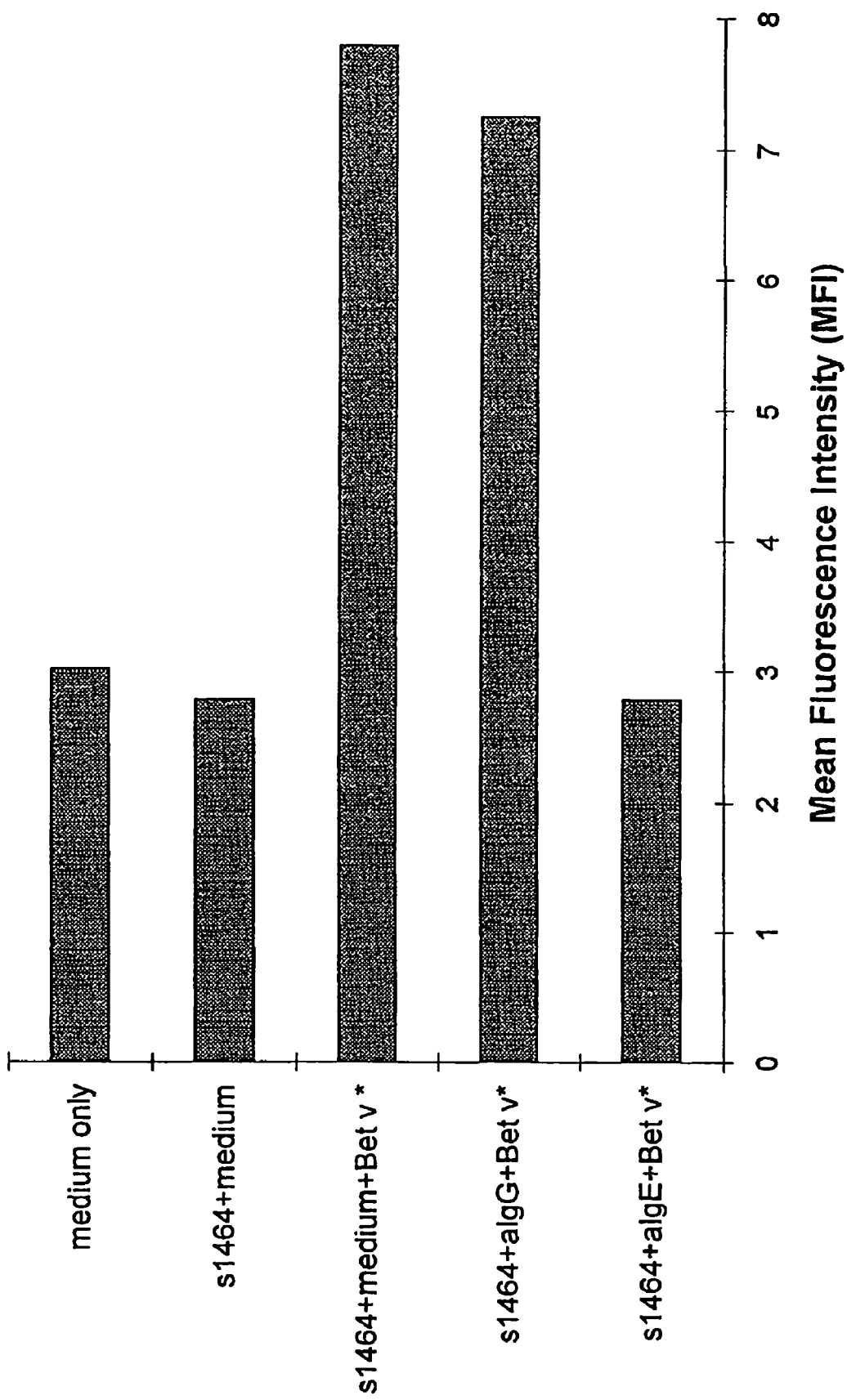

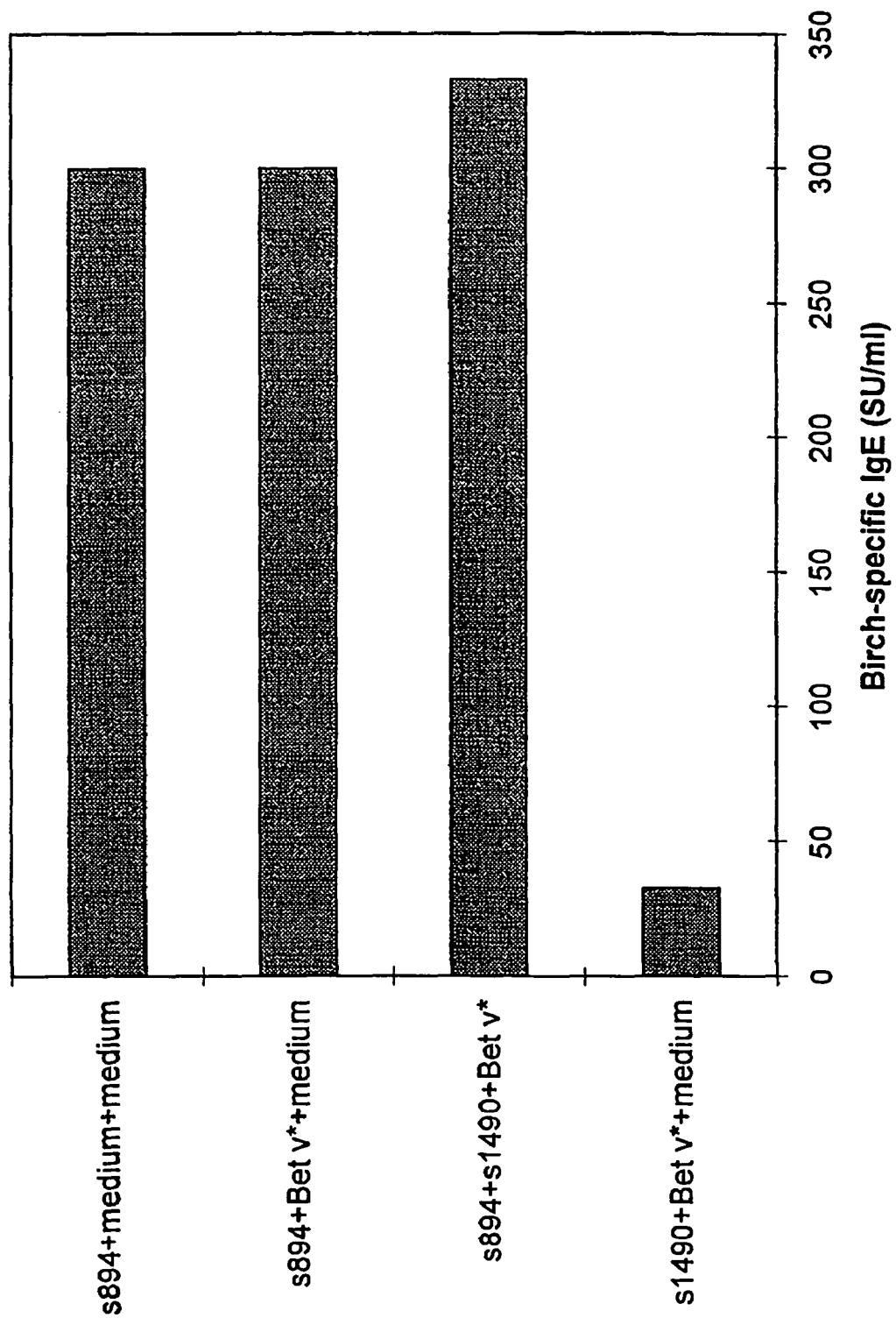

CD23-based immunoassay for the detection of allergen-specific IgE b) direct assay

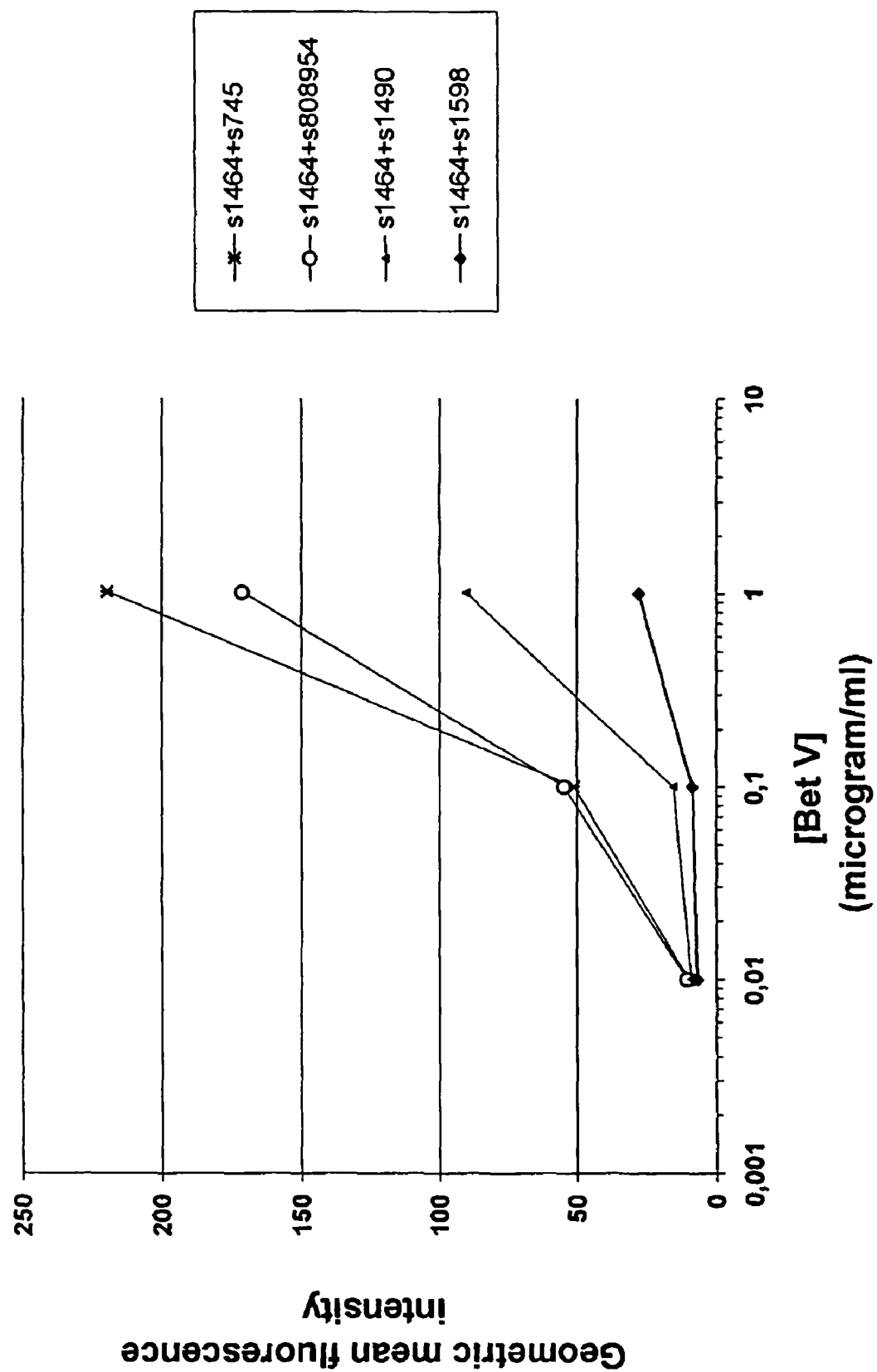

METHOD OF DETECTING AND/OR QUANTIFYING A SPECIFIC IGE ANTIBODY IN A LIQUID SAMPLE

This application claims priority from provisional application 60113536 filed Dec. 22, 1998 and claims foreign priority to PA199801709 filed Dec. 22, 1998.

The present invention relates to a method of detecting and/or quantifying an IgE antibody specific to a ligand in the form of antigen, antibody or hapten in a liquid sample.

WO 94/11734 describes a two-site immunoassay for an antibody using a chemiluminescent label and a biotin bound ligand, said method comprising the steps of (a) mixing the liquid sample with a ligand antigen, antibody or hapten bound to biotin or a functional derivative thereof, an antibody directed against the antibody to be detected bound to paramagnetic particles and a chemiluminescent acridinium compound bound to avidin, streptavidin or a functional derivative thereof to form a solid phase complex, (b) magnetically separating the a solid phase from the liquid phase, (c) initiating a chemiluminescent reaction, if any, in the separated solid phase and (d) analysing the separated solid phase for the presence of a chemiluminescent phase, which is indicative of the presence of said antibody in the sample.

The prior art method is particularly suitable for measuring the concentration of specific immunoglobulins in body fluids, such as a specific immunoglobulin selected from the group of IgA, IgD, IgE, IgG, IgM and subclasses thereof.

The prior art method is also suitable for the detection and quantification of the total content of immunoglobulins in a class or subclass, such as IgA, IgD, IgE, IgG, IgM and subclasses thereof.

WO 98/23964 discloses a method of detecting canine, feline and equine IgE. One embodiment of the method comprises the steps of a) binding human Fcε receptor (FcεRI) to a substrate, b) contacting the substrate-FcεRI with an IgE-containing composition to form a complex of substrate-FcεRI-IgE, c) removing excess non-bound material, d) adding an indicator molecule in the form of e.g. an antigen, which can selectively bind to the IgE of the complex, wherein said indicator molecule may be conjugated to a detectable marker, e.g. a fluorescent label or a ligand, such as biotin, e) removing excess indicator molecule and f) measuring the labelled complex formed.

Elsewhere in the document it is generally mentioned that the substrate may be e.g. a particulate material, including magnetic particles, or a recombinant cell expressing the FcεRI. Also it is generally mentioned that the detectable marker may be a chemiluminescent label.

The prior art assay disclosed in WO 98/23964 uses an excess of substrate-FcεRI and hence measures the full content of the specific IgE to be detected as well as other immunoglobulins, e.g. IgG, which may bind to the FcεRI used. The assay is carried out in strict in vitro conditions involving washing steps after addition of serum to substrate-FcεRI as well as after addition of antigen.

The article "Regulation and targeting of T-cell immune responses by IgE and IgG antibodies", Bheekha Escura et al., Immunology, Vol. 86, 343-350, 1995, discloses a method comprising the steps of a) incubating mouse/human chimeric monoclonal IgE specific to NIP (5-iodo-4-hydroxyl-3-nitrophenacetyl) with allergen-NIP to form a complex, b) incubating the complex with B cells, c) removing excess complexes by washing and d) incubating the resulting cells with fluorescence labelled antibody against the NIP specific antibody, and e) detecting the fluorescence.

WO 99/51988, which was published after the priority date of the present application, discloses a method of detecting a biologically active, allergen-specific immunoglobulin using a Fc epsilon receptor I molecule comprising forming a complex of FcεRI-immunoglobulin-allergen and detecting the complex formed. The document mentions preferred embodiments, wherein allergen conjugated to a plastic bead particle and the immunoglobulin-containing sample is contacted to allow for formation of a substrate-bound immunoglobulin-allergen complex, and wherein the said complex is contacted with FcεRI.

SUMMARY OF THE INVENTION

The technical problem addressed by the present invention is to provide a method of detecting and/or quantifying a specific IgE antibody in a liquid sample, which allows the binding reactions between the various reactants to be carried out in more in vivo like conditions so as to give an IgE measurement that reflects the ability of IgE to exert its effector functions through binding to its receptor rather than just measuring the presence of IgE in a sample.

The method of the present invention is characterized in comprising the steps of (a) contacting (i) the sample with (ii) a free ligand in the form of an antigen, an antibody or a hapten to form a mixture I comprising IgE-containing complexes, (b) mixing mixture I with a carrier to which is bound (iii) IgE receptor, said IgE receptor being CD23 (FcεRII) and/or FcεRI, to form a mixture II comprising carrier-bound IgE-containing complexes, (c) separating the carrier-bound IgE-containing complexes from mixture II, and (d) determining the amount of the carrier-bound IgE-containing complexes formed.

The low affinity IgE receptor CD23 (FcεRII) is found on the surface of eosinophils, activated B and T cells and dendritic cells. CD23 is a multifunctional receptor, which has been shown to play an important role in IgE-mediated antigen presentation. It is believed that CD23 primarily binds IgE present in the form of multi-component complexes containing both IgE and antigen/allergen (1, 2). However, there have been reports that NIP-specific monoclonal IgE in monomeric form can bind to CD23 (3). However, it cannot be excluded that aggregation of the purified monoclonal IgE antibody takes place. CD23 consists of an α-chain, and it may be present as a monomer, a dimer or a trimer.

The high affinity IgE receptor FcεRI is found on the surface of mast cells and basophils, and also on Langerhans cells, monocytes and dendritic cells. FcεRI has also been shown to play a role in IgE-mediated antigen/allergen presentation (4). IgE may bind to FcεRI in the form of monomeric IgE, IgE-antigen/allergen and multi-component complexes containing both IgE and antigen/allergen. FcεRI on mast cells and basophils consists of an α-chain, a β-chain and a γ-chain, and FcεRI on Langerhans cells, monocytes and dendritic cells consists of an α-chain and a γ-chain.

The present invention is based on the recognition that it is possible to use CD23 in an antibody detecting assay provided that the IgE-containing sample is allowed to react with the antigen/allergen before, or at the latest simultaneously with, the binding to CD23.

The present invention is further based on the recognition that in general an assay procedure, wherein the IgE-containing liquid sample is allowed to react with the antigen/allergen in dissolved state in a first step, and wherein the complete resulting mixture is contacted with the carrier-IgE receptor, simulates closely the conditions, in which the identical reactions take place in vivo.

In particular, the assay of the invention simulates any interference from other immunoglobulins, as well as any other potentially interfering component, present in the sample, which may take place during the formation of the multi-component complexes containing IgE and antigen/allergen as well as during the formation of IgE-antigen/allergen. Also, it is possible that interference from other ingredients of the resulting mixture also takes place in the binding between carrier-IgE receptor on the one hand and monomeric IgE, IgE-antigen/allergen and the multi-component complexes containing IgE and antigen/allergen.

Thus, the assay of the invention makes it possible to measure the level of specific IgE, which in in vivo conditions is able to bind to the CD23 and/or FcεRI receptors thereby exerting its biological function. In the following, this is referred to as the relevant in vivo level of IgE. An achievement of the present invention is the recognition that such a measurement of the relevant in vivo level of IgE holds valuable information about the subject from which the sample is taken, since it is the ability of the IgE present to bind to the IgE receptors rather than the total level of IgE, which determines the immunological status of the said subject. Thus, the assay of the invention has provided a possibility of determining the immunological status of the subject much more accurately than with prior art assays.

In particular, the assay of the invention is valuable in connection with the monitoring and the evaluation of the immunological status of subjects receiving Specific Allergy Vaccination (SAV) treatment. Thus, it has been shown that SAV treatment results in an inhibition or reduction of the binding of IgE to IgE receptors, and hence the relevant in vivo level of IgE gives a much more precise measure of the severity of the allergic disease than the total IgE level in as much as the two said levels may differ significantly. For example, the in vivo level of IgE as determined by the method of the invention before and after SAV treatment may differ by a factor four, whereas in comparison the IgE level measured by a conventional IgE assay is unchanged before and after SAV treatment.

The present invention further relates to the use of the method of any of claims 1-13 to monitor and evaluate the immunological status of subjects, in particular humans, including both allergic and non-allergic subjects.

In particular, the present invention relates to the use of the method of any of claims 1-13 to monitor and evaluate the immunological status of subjects, in particular humans, receiving Specific Allergy Vaccination (SAV) treatment.

DETAILED DESCRIPTION OF THE INVENTION

In an embodiment of the invention the ligand is labelled.

The expression "labelled ligand" means any ligand comprising a labelled atom or part, e.g. a radioactive atom label.

In another embodiment of the invention the ligand used in step a) is bound to (iv) a label compound. In a further embodiment of the invention, (iv) a label compound is added in step a) in addition to (i) the sample and (ii) the ligand. Also, (iv) a label compound may be added to the IgE-containing complexes formed in step a).

In a preferred embodiment of the invention (iv) a label compound is added to the carrier-bound IgE-containing complexes formed in step (b).

In a particularly preferred embodiment of the invention (iv) a label compound is added to the carrier-bound IgE-containing complexes resulting from the separation step (c) to form a mixture II', in which case the resulting labelled and carrier-bound IgE-containing complexes are separated from mixture II' and washed prior to step (d).

The expression "label compound" means any suitable label system conventionally used in immunoassays comprising luminescent labels, chemiluminescent labels, enzyme labels, radioactivity labels, fluorescent labels, and absorbance labels.

In a preferred embodiment of the invention, the (iv) label compound is a chemiluminescent compound covalently bound to avidin, streptavidin or a functional derivative thereof.

The chemiluminescent label is preferably an acridinium compound, such as N-hydroxy-succinimide dimethylacridiniumester (NHS-DMAE). Avidin/streptavidin and DMAE may be coupled according to the methods of Weeks et al., Clinical Chem., Vol. 29, 1474-1479 (1983). Other examples of chemiluminescent compounds suitable for use in the present invention are luminol, lucigenin and lophine.

In another preferred embodiment of the invention, the (iv) label compound is a fluorescent label covalently bound to avidin, streptavidin or a functional derivative thereof. A preferred example of a fluorescent label is phygoerythrine (PE).

Depending on the type of label system used, the label compound may be bonded directly to the ligand or it may be coupled to the ligand by means of biotin. In a preferred embodiment of the invention the ligand is bound to biotin or a functional derivative thereof. Biotin is preferably bound to the ligand added in step (a).

The label compound may also be coupled to the IgE to be detected by means of an antibody to the IgE, wherein the antibody to IgE is coupled to IgE in such a manner that the binding of the IgE to the IgE receptor is not hindered. The combination of the label compound and the detecting antibody is preferably added to the carrier-bound IgE-containing complexes formed in step (b) or (c). Alternatively, the combination of the label compound and the detecting antibody is added previously either simultaneously with the sample and the ligand in step (a) or it is added to the IgE-containing complexes formed in step (a).

The detecting antibody is preferably a polyclonal antibody.

The use of a detection system consisting of a detecting antibody coupled to a label compound has the advantage that the same system may be used independently of the IgE to be detected. Also, it is believed that it is advantageous to use a detection system, which allows the use of a non-labelled ligand, since this best resembles in vivo conditions.

Depending on the type of label system used, the label compound may be bonded directly to the detecting antibody or it may be coupled to the detecting antibody by means of biotin. In a preferred embodiment of the invention the detecting antibody is bound to biotin or a functional derivative thereof. Biotin is preferably bound to the detecting antibody added after step (c).

Preferably, the IgE-containing sample is contacted with the ligand and allowed to incubate to form a mixture I (step (a)) before contacting mixture I with the carrier/IgE receptor (step (b)). The duration of the incubation of the sample and the ligand may be from 1 to 120, preferably 5 to 60, more preferably 10 to 40, minutes.

It is believed that this procedure simulates the in vivo conditions the best, since it allows complexes of ligand and IgE to be formed prior to contact with the IgE receptor, and since CD23 binds IgE in the form of the said complexes.

Alternatively, step (a) and (b) are carried out simultaneously in one operation, i.e. the IgE-containing sample, the ligand and carrier-IgE receptor are mixed and incubated together. In this case the duration of the incubation may be from 1 to 120, preferably 5 to 60, more preferably 10 to 30, minutes.

The carrier may be any solid material commonly used in immunological assays, such as a biological cell, e.g. a B cell; a particulate material composed of e.g. glass, a metal, i.a. iron, or a polymer; a paramagnetic particle; and a plate, a well, a dish or a tube composed of a polymer.

The carrier is preferably a particle, most preferably a paramagnetic particle. The term "paramagnetic particle" means any paramagnetic particle, which may be dispersed or suspended in a liquid medium, e.g. "Biomag" particles (iron oxide particles coated with amine terminated groups) sold by Advanced Magnetics Inc., U.S.A., and "Dynabeads" (iron oxide covered with a polymer) sold by Dynal A.S., Norway.

When a particulate material is used as carrier, the separation of the solid phase complex from the liquid phase may, depending on the type of solid particle used, be carried out by i.a. magnetic separation, filtration, sedimentation, centrifugation, chromatography, column chromatography.

In a preferred embodiment of the invention the IgE to be detected is quantified using both CD23 alone to obtain a first measurement and using FcεRI alone to obtain a second measurement.

CD23-mediated antigen presentation at low antigen concentrations via B cells facilitates activation of $CD4^+$ T cells, which play an important role in late phase allergic responses, i.e. in responses appearing between about 6 and 24 hours upon exposure. FcεRI-triggering of mast cells and basophils after cross-linking of IgE causes the immediate allergic responses. Thus, the biological functions of CD23 and FcεRI are different, and hence the results obtained with the assay of the invention using as IgE receptor CD23 and FcεRI, respectively, hold different information about the immunological status of the subject, from which the IgE-containing samples originate. It is therefore advantageous to obtain results for both CD23 and FcεRI in order to provide a more complete basis for monitoring and evaluating the immunological status of the subject.

In another preferred embodiment of the invention a combination of CD23 and FcεRI is used. In case the carrier used is a particulate material, CD23 and FcεRI may be bound to separate particles or to the same particles.

The method of the invention may be carried out using an excess of ligand compared to expected IgE level in the sample. It is possible to use a large excess of ligand, e.g. a ratio of ligand to IgE of up to 10000.

In a further preferred embodiment of the invention the number of ligand molecules is between 100% and 10.000%, preferably between 100% and 1000%, more preferably between 100% and 200%, more preferably between 100% and 150%, and most preferably between 100% and 120%, of the number of IgE molecules to be detected.

As will appear from the above it is preferred that the ligand and the IgE is mixed in amounts of corresponding magnitude or with a moderate excess of ligand. This is preferred because it is believed that this corresponds to in vivo conditions, wherein complex formation is favoured.

The preferred ratio of ligand to IgE depends on a number of factors, such as the type of carrier, the characteristics of the IgE to be detected, and the characteristics of the IgE receptor and ligand corresponding to the IgE to be detected, and it should therefore be optimised for the specific assay to be carried out. However, it is in general preferred that the ratio is within the limits mentioned above, since the best results with respect to measuring the relevant in vivo level of IgE are obtained with such a ratio. It is believed that the explanation for this is that as mentioned above CD23-mediated antigen presentation is a mechanism that enhances antigen presentation at low antigen concentrations. At high antigen concentrations the said mechanism becomes irrelevant, because enough antigen will be presented by antigen presenting cells even without specific capture by CD23. In other words, it is believed that the complexes of ligand and IgE bind to both CD23 and to FcεRI, and that the equilibrium is shifted towards binding to CD23 at the ratios of ligand to IgE mentioned above.

Preferably, the method of the invention is carried out at a temperature of from 0° C. to 100° C., more preferably 0° C. to 40° C., and most preferably 20° C. to 38° C.

If biological cells are used as carrier, and if a detection system consisting of a detecting antibody coupled to a label compound is used, then the assay is preferably carried out at a relatively low temperature of from 0° C. to 10° C., more preferably 0° C. to 6° C., in order to avoid that complexes of IgE and allergen bound to IgE receptors on the outer surface of the cell are internalised into the interior of the cell before labelling has taken place, which would lead to incorrect measurements.

The present invention in particular relates to a method of detecting and/or quantifying a specific IgE antibody in a liquid sample comprising the steps of (a) contacting (i) the sample with (ii) a free ligand in the form of an antigen, an antibody or a hapten to form a mixture I comprising IgE-containing complexes, wherein the ligand is bound to biotin or a functional derivative thereof, (b) mixing mixture I with a carrier to which is bound (iii) IgE receptor, said IgE receptor being CD23 (FcεRII) and/or FcεRI, to form a mixture II comprising carrier-bound IgE-containing complexes, (b') separating the carrier-bound IgE-containing complexes from mixture II and washing the said complexes, (b") adding to the washed carrier-bound IgE-containing complexes a solution of (iv) a chemiluminescent compound covalently bound to avidin, streptavidin or a functional derivative thereof to form a mixture II', (c) separating the carrier-bound IgE-containing complexes from mixture II' and washing the said complexes, (d) initiating a chemiluminescent reaction in the resulting IgE-containing complexes and detecting/measuring the resulting chemiluminescence, if any.

DEFINITIONS

In the present invention the expression "specific IgE antibody" means any specific immunoglobulin of the IgE isotype as well as any other immunoglobulin, which has an affinity for the IgE receptors CD23 and/or FcεRI.

The term "liquid sample" means any liquid or liquefied sample, including solutions, emulsions, dispersions and suspensions. The sample may be a biological fluid, such as blood, plasma, serum, urine, saliva and any other fluid, which is excreted, secreted or transported within a biological organism.

The expression "ligand in the form of an antigen, an antibody or a hapten" may be any immunologically active substance. "Antigen" may be an allergen, e.g. pollen from trees, grass, weeds etc., mold allergens, allergens from acarids (mites) and animals, such as cat, dog, horse, cattle and bird, allergens of stinging insects and inhaled allergens of insects, and food allergens; "antibody" may be a monoclonal or polyclonal antibody, including recombinant and fragmented antibodies; and "hapten" may be carbohydrate moieties or fragments thereof, enzyme inhibitors or drugs, e.g. penicillin or a derivative thereof.

In connection with the present invention the term "IgE receptor" means CD23 (FcεRII) and/or FcεRI. The term "CD23" means any formulation thereof and any part thereof, including CD23 in pure form or in a mixture, solution or extract; synthetic or recombinant CD23; CD23 originating from natural sources; and whole CD23 and parts thereof. The α-chain of CD23 may be used as a trimer, a dimer or a monomer, and only the α-chain or the soluble part thereof, i.e. the part extending from the outer surface of the cell membrane, or a section of the soluble part of the α-chain may be used as CD23. "FcεRI" means any formulation thereof and any part thereof, including FcεRI in pure form or in a mixture, solution or extract; synthetic or recombinant FcεRI; FcεRI originating from natural sources; and whole FcεRI and parts thereof. In particular, only the α-chain, which is primarily responsible for the binding of IgE, or the soluble part thereof, i.e. the part extending from the outer surface of the cell membrane, or a section of the soluble part of the α-chain may be used as FcεRI.

The expression "free ligand" means a ligand, which is free to unhindered form complexes with IgE. The expression "free ligand" includes ligands in solution, ligands coupled to a substance in solution, ligands coupled to a semi-solid substance in suspension and ligands coupled to a solid carrier in suspension.

The present invention is described in further detail with respect to the drawings, wherein FIG. 1a shows the fluorescence level measured in an assay of the invention using (i) no serum and no allergen, (ii) a control serum and allergen, and (iii) allergic patient serum and allergen.

FIG. 1c shows the fluorescence level measured in an assay of the invention using (i) no serum and no allergen, (ii) allergic patient serum and no allergen, (iii) allergic patient serum and allergen, (iv) allergic patient serum, allergen and antibody to IgG, and (v) allergic patient serum, allergen and antibody to IgE.

FIG. 2b shows the IgE level of situations (i)-(iv) of FIG. 2a calculated on the basis of measurements of the IgE level of allergic patient serum and SAV-treated allergic patient serum in a reference total IgE assay.

Figure 3:
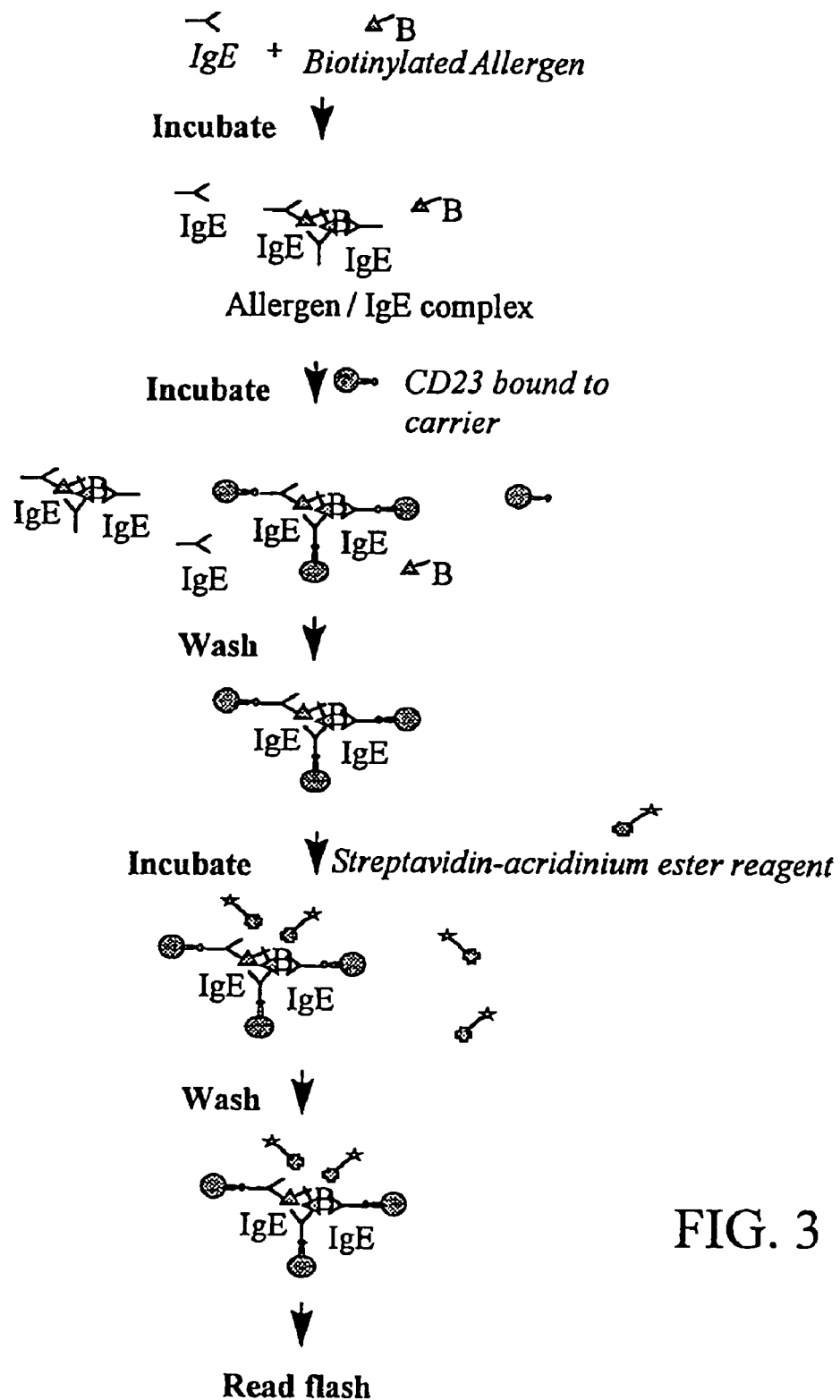
Figure 4:
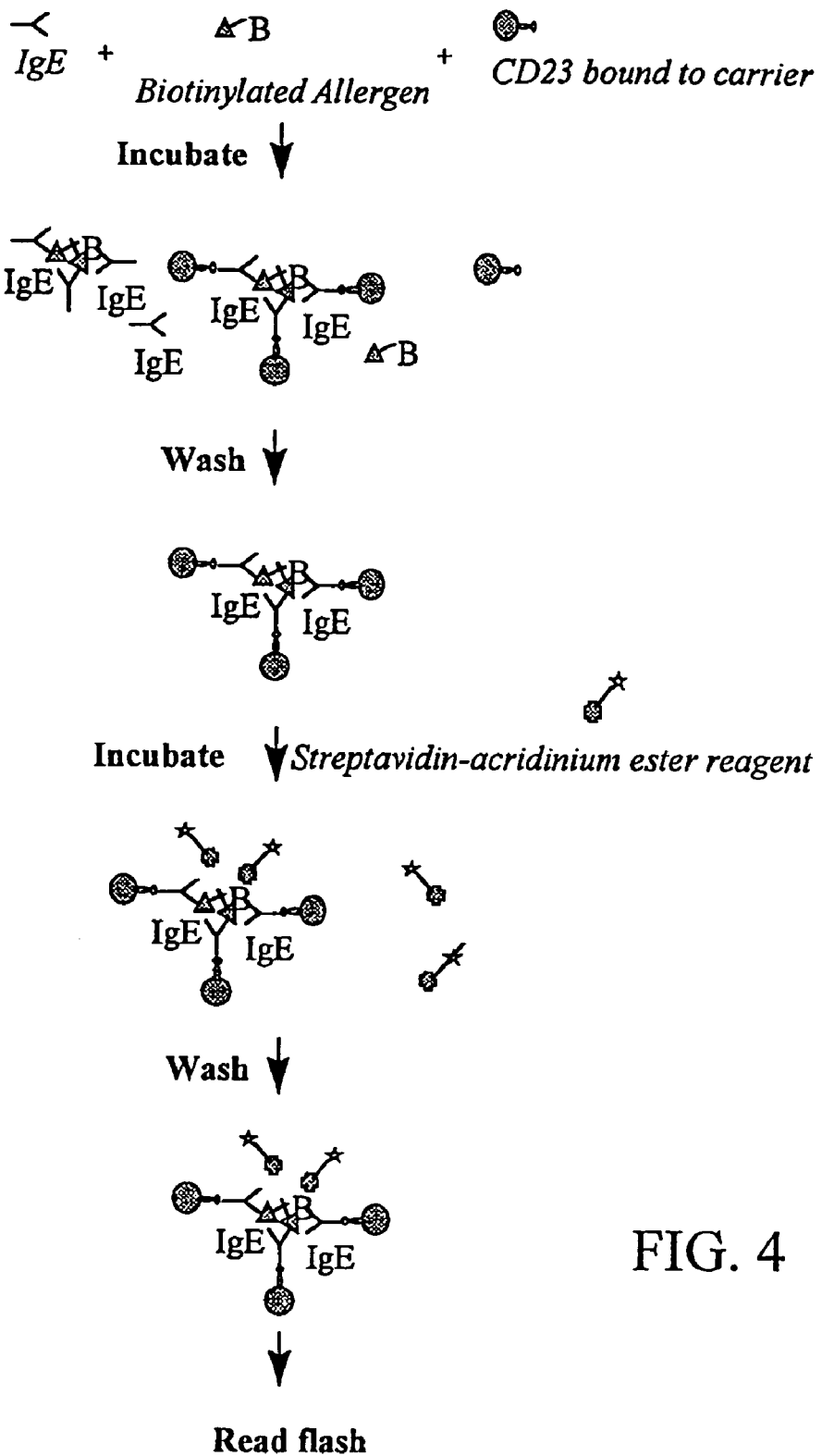
Figure 5:
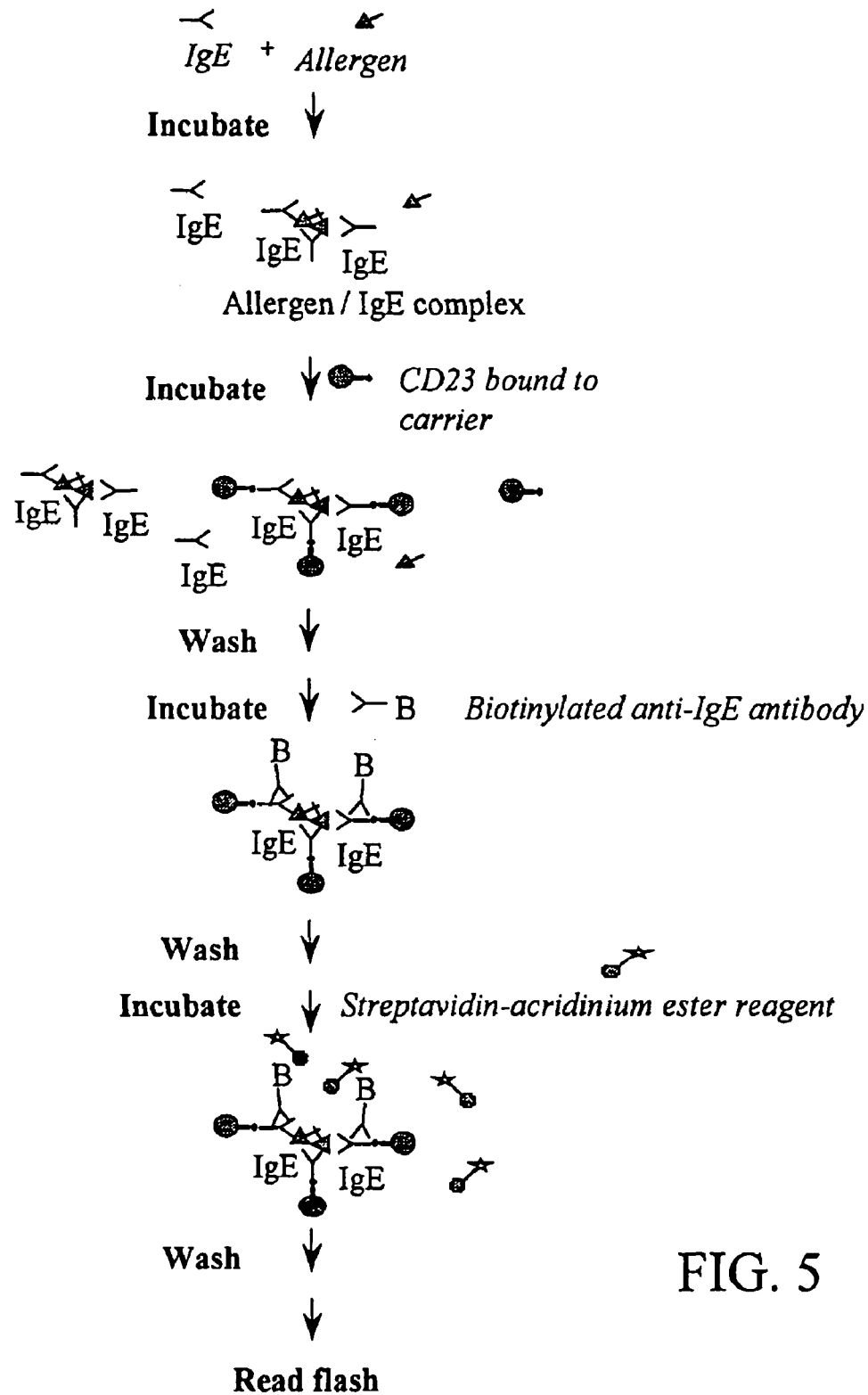
Figure 6:
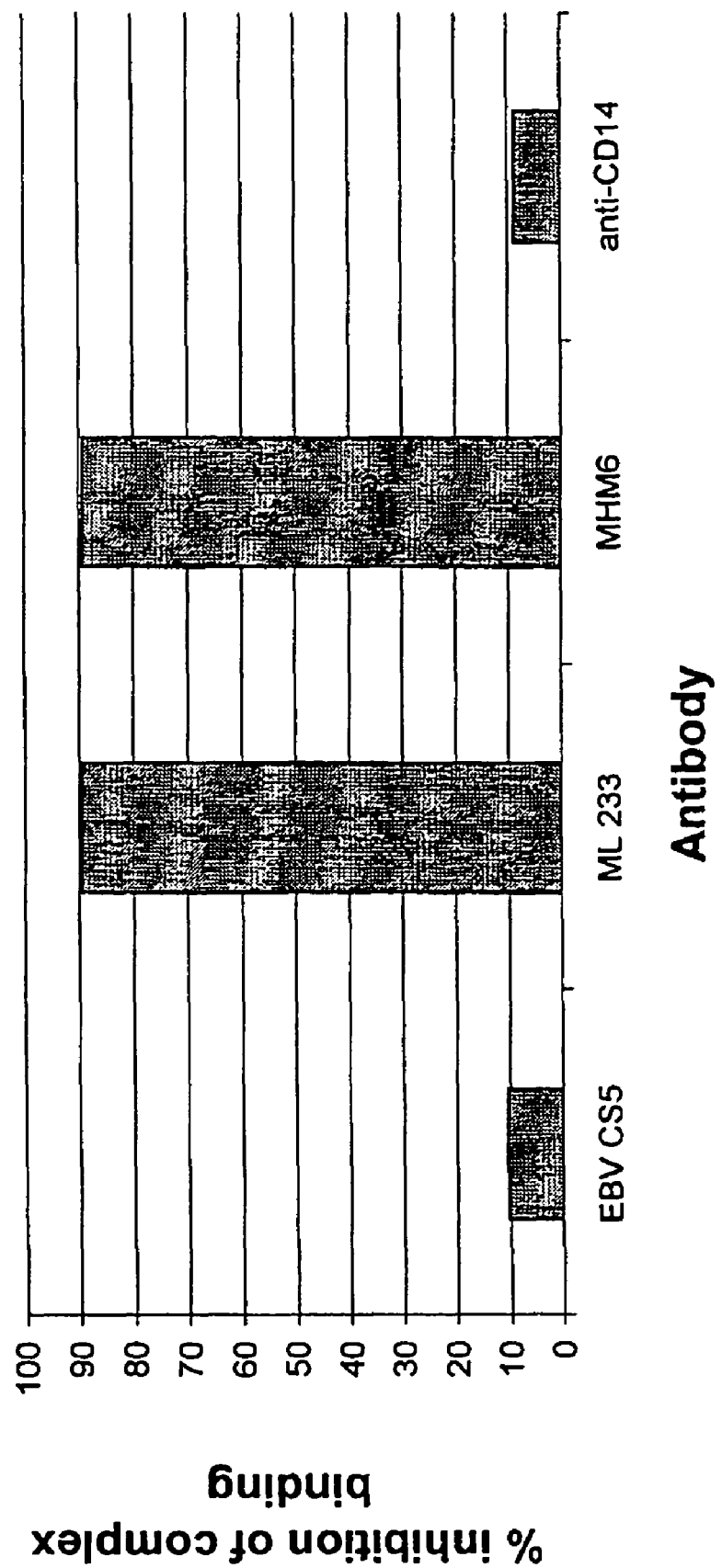

FIG. 3 is a diagrammatic representation of one preferred embodiment of the invention FIG. 4 is a diagrammatic representation of a second preferred embodiment of the invention FIG. 5 is a diagrammatic representation of a third preferred embodiment of the innovation FIG. 6 shows the fluorescence level measured in an assay of the invention using (i) allergic patient serum, allergen and antibody (1) directed to the IgE binding moiety of CD23, (ii) allergic patient serum, allergen and antibody (2) directed to the IgE binding moiety of CD23, (iii) allergic patient serum, allergen and antibody directed at the non-IgE binding moiety of CD23, and (iv) allergic patient serum, allergen and antibody to CD14.

Figure 7A:
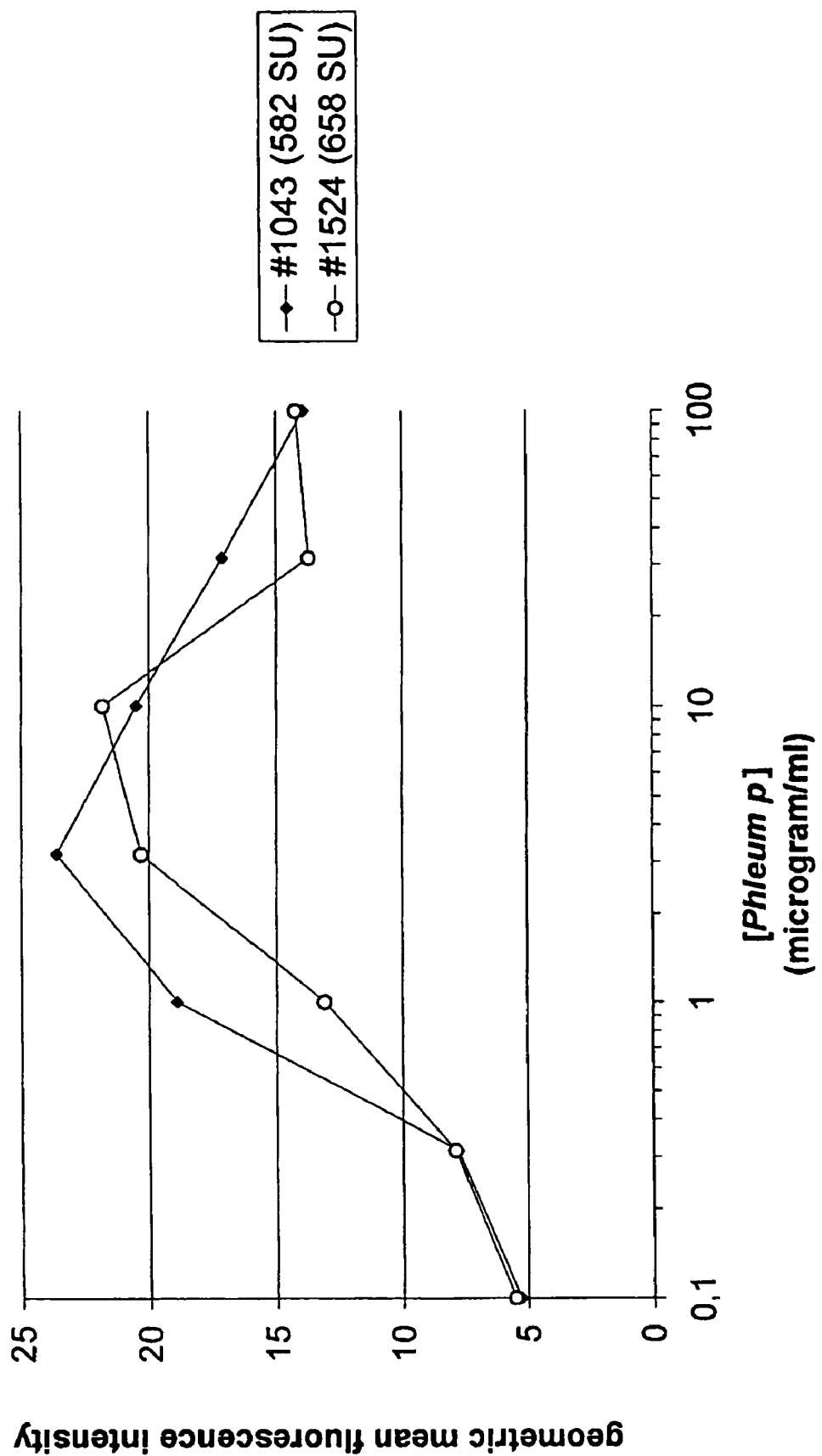
Figure 7B:
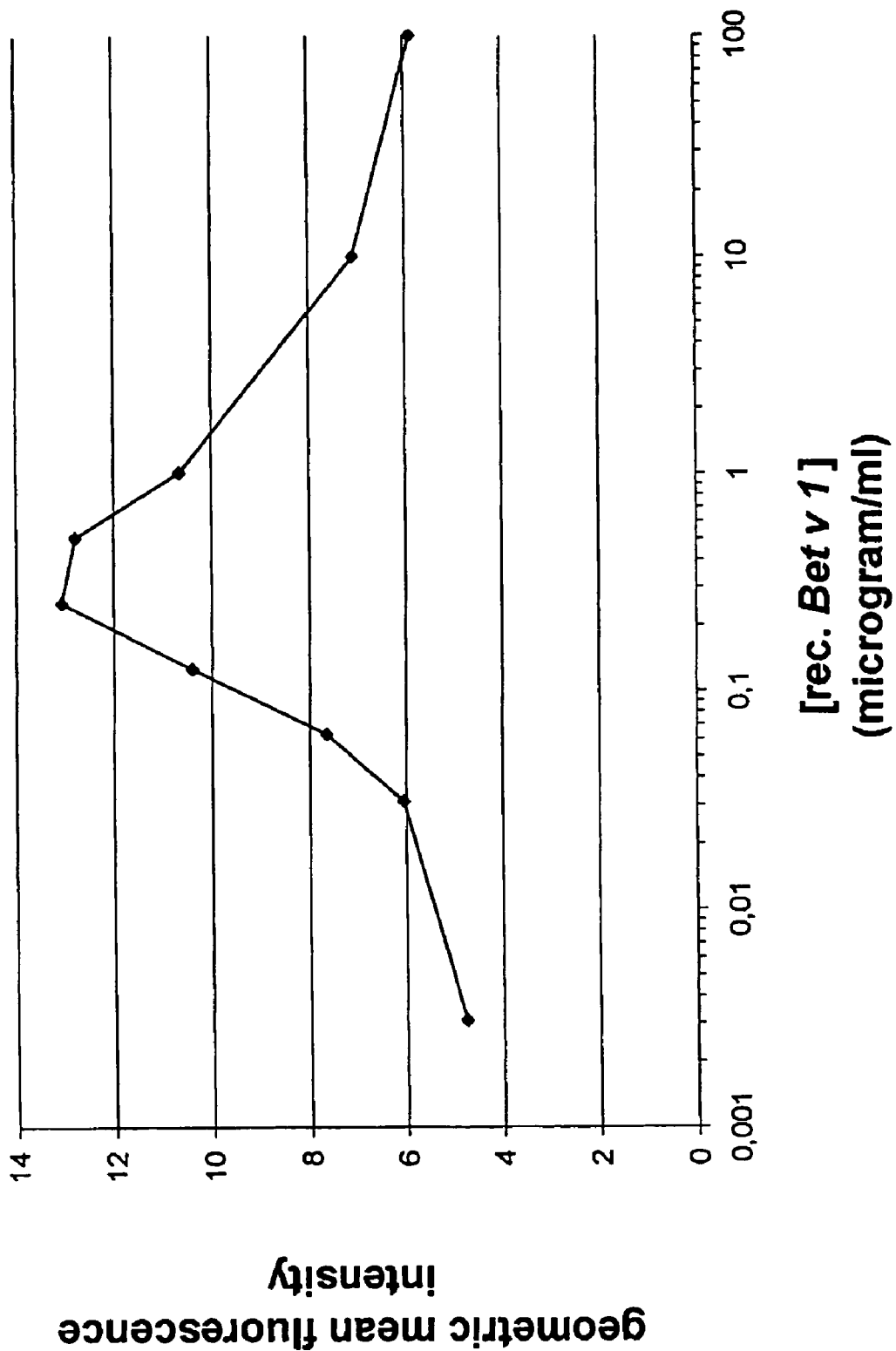

FIG. 7a shows the fluorescence level as measured in an assay of the invention using allergic patient serum and increasing doses of grass allergens FIG. 7b shows the fluorescence level measured in an assay of the invention using allergic patient serum and increasing doses of a purified, recombinantly expressed major birch allergen FIG. 8a shows the fluorescence level measured in an assay of the invention using increasing doses of birch allergens and (i) birch allergic patient serum and non-allergic control serum, (ii) allergic patient serum and serum from a SAV-treated birch allergic patient (A), (iii) birch allergic patient serum and serum from a SAV-treated birch allergic patient (B), and (iv) birch allergic patient serum and serum from a SAV-treated grass allergic patient.

Figure 8B:
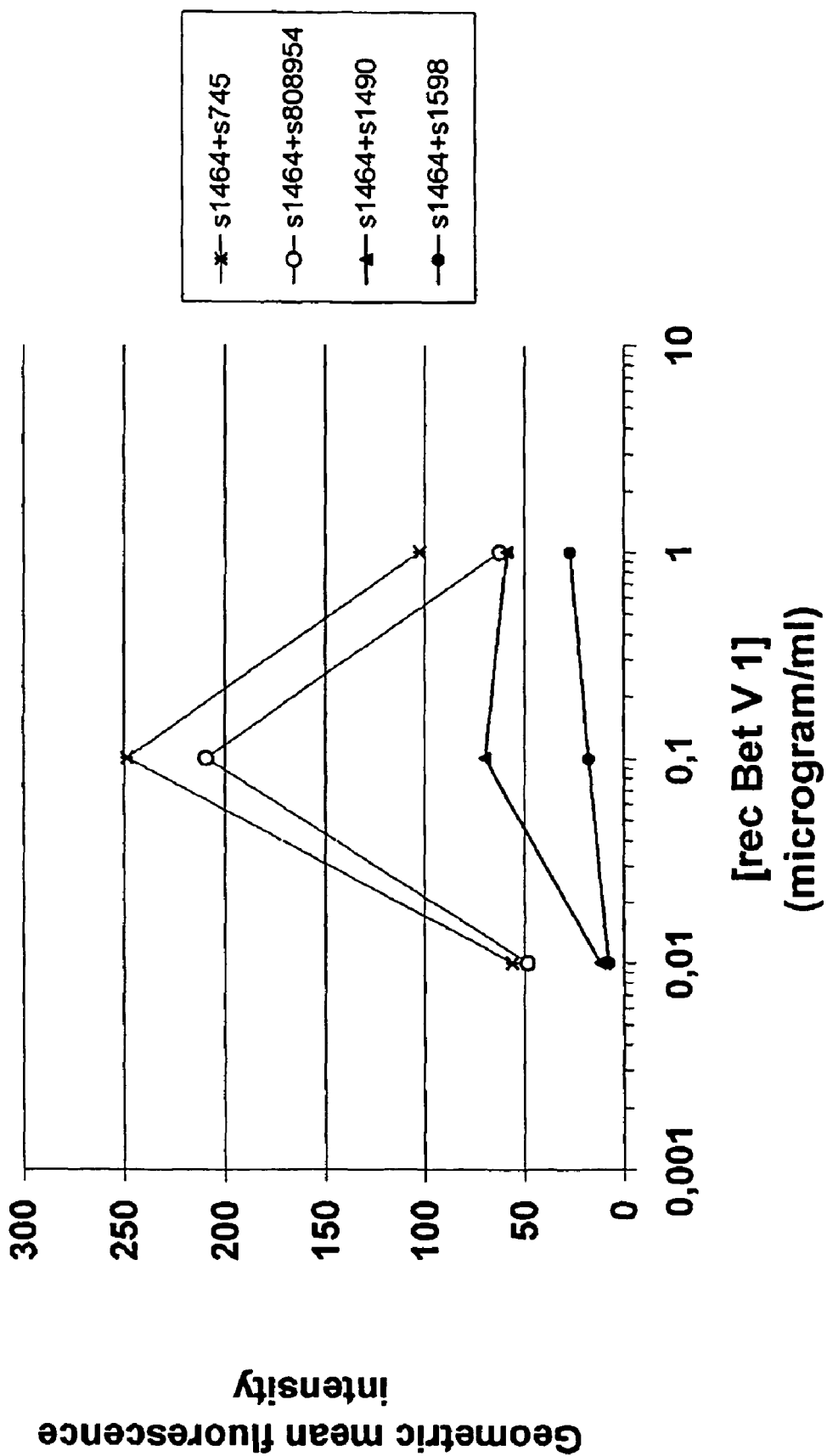

FIG. 8b shows the fluorescence level measured in an assay of the invention using increasing doses of a purified, recombinantly expressed major birch allergen, and (i) birch allergic patient serum and non-allergic control serum, (ii) allergic patient serum and serum from a SAV-treated birch allergic patient (A), (iii) birch allergic patient serum and serum from a SAV-treated birch allergic patient (B), and (iv) birch allergic patient serum and serum from a SAV-treated grass allergic patient.

FIG. 3 shows the steps of a preferred embodiment of the assay of the invention in principle. In a first step a biotinylated allergen and a sample containing IgE specific to the allergen (designated "IgE" in the figure) are mixed and incubated to form a mixture I containing complexes including a number of IgE molecules and a number of allergen molecules, the mixture I further comprising excess IgE and allergen. In a second step, a particulate carrier to which a number of CD23 molecules (and/or a number of FcεRI molecules) are bound is added, and the said complexes are bound to the carrier via CD23 to form a mixture II. Possibly, a smaller amount of IgE may bind to CD23 in monomeric form. In a third step, the carrier-bound complexes are separated from mixture II and washed one or more times to remove non-bound reactants. Also, the washing will remove any non-bound complexes, which may be present, since as mentioned above it is possible that the interference taking place in the present assay is the result of an inhibition of the binding of complexes to the IgE receptor. The separation of the complexes from mixture II may e.g. be carried out by magnetic separation, if paramagnetic particles are used as carrier. A chemiluminescent label, preferably a streptavidin-acridinium ester reagent, is incubated with the carrier-bound complexes to bind the label to the complex-bound biotin. Following the incubation the carrier-bound, labelled complexes are separated and washed to remove non-reacted label molecules, and the chemiluminescent reaction is started by use of a suitable reagent, e.g. sodium hydroxide, and the chemiluminescence of the carrier-bound, labelled complexes is measured.

FIG. 4 shows the steps of a preferred embodiment of the assay of the invention in principle. In a first step a biotinylated allergen, a sample containing IgE specific to the allergen (designated "IgE" in the figure) and a particulate carrier to which a number of CD23 molecules (and/or a number of FcεRI molecules) are bound, are mixed and incubated to form a mixture II containing carrier-bound complexes including a number of IgE molecules and a number of allergen molecules, the mixture II further comprising excess IgE and allergen as well as non-bound complexes. Then, the carrier-bound complexes are separated from mixture II and washed one or more times.

Subsequently, a chemiluminescent label, preferably a streptavidin-acridinium ester reagent, is incubated with the carrier-bound complexes to bind the label to the complex-bound biotin. Following the incubation the carrier-bound, labelled complexes are separated and washed to remove non-reacted label molecules, and the chemiluminescent reaction is started by use of a suitable reagent, e.g. sodium hydroxide, and the chemiluminescence of the carrier-bound, labelled complexes are measured.

FIG. 5 shows the steps of another preferred embodiment of the invention. In a first incubation step an allergen and a sample containing IgE specific to the allergen (designated "IgE" in the figure) are mixed and incubated to form a mixture A containing complexes including a number of IgE molecules and a number of allergen molecules, the mixture A further comprising excess IgE and allergen. In a second incubation step, a particulate carrier to which a number of CD23 molecules (and/or a number of FcεRI molecules) are bound is added, and the said complexes are bound to the carrier via CD23 to form a mixture B. Possibly, a smaller amount of IgE may bind to CD23 in monomeric form. Subsequently, the carrier-bound complexes are separated from mixture B and washed one or more times to remove non-bound reactants. Also, the washing will remove any non-bound complexes, which may be present, since as mentioned above it is possible that the interference taking place in the present assay is the result of an inhibition of the binding of complexes to the IgE receptor. The separation of the complexes from mixture B may e.g. be carried out by magnetic separation, if paramagnetic particles are used as carrier. In a third incubation step biotinylated antibody to the IgE (detecting antibody) is added to form a mixture C. The detecting antibody is polyclonal and will bind to all IgE's regardless of the specificity of the IgE. The resulting carrier-bound complexes are separated from the mixture C, and the said complexes are washed. In a fourth incubation step, a chemiluminescent label, preferably a streptavidin-acridinium ester reagent, is incubated with the carrier-bound complexes to bind the label to the complex-bound biotin. Following the incubation the carrier-bound, labelled complexes are separated and washed to remove non-reacted label molecules, and the chemiluminescent reaction is started by use of a suitable reagent, e.g. sodium hydroxide, and the chemiluminescence of the carrier-bound, labelled complexes is measured.

In the following, the invention is described in further detail with reference to the Examples.

EXAMPLES

In the examples the following abbreviations are used:

FITC: Fluorescein isothiocyanat

EBV: Epstein Barr virus

SU: Standard Units

SAV: Specific Allergy Vaccination

Example 1

Detection of the binding of birch allergen-specific IgE to CD23 expressed by EBV-transformed B cells by flowcytometric analysis.

FITC-labelled *Betula verrucosa* (Bet v) extract (1 µg/ml) was incubated with control serum 734 (no detectable IgE in a reference assay measuring the total content of IgE (MagicLite®, ALK-ABELLÒ, Hoersholm, Denmark)), or with birch allergic patient serum 1464 (>800 SU/ml birch-specific IgE in MagicLite® assay) at a final serum concentration of 60%. EBV transformed B cells from an allergic patient in culture medium were added to a final concentration of $4 \times 10^6$/ml and incubated for 1 hour at 37° C., followed by two washes to remove excess allergen. After washing the cells, binding of FITC-labelled Bet v (Bet v*) to the B cells was analysed by measuring fluorescence using a FACSCalibur flowcytometer.

The results are shown in FIG. 1a, wherein the Mean Fluorescence Intensity (MFI) is indicated for (i) no serum and no Bet v (Background) designated "Medium only" in FIG. 1a, (ii) s734 and Bet v, and (iii) s1464 and Bet v. The results demonstrate that the binding of FITC-labelled birch allergen extract to B lymphocytes that express CD23 can be demonstrated directly.

Figure 1B:
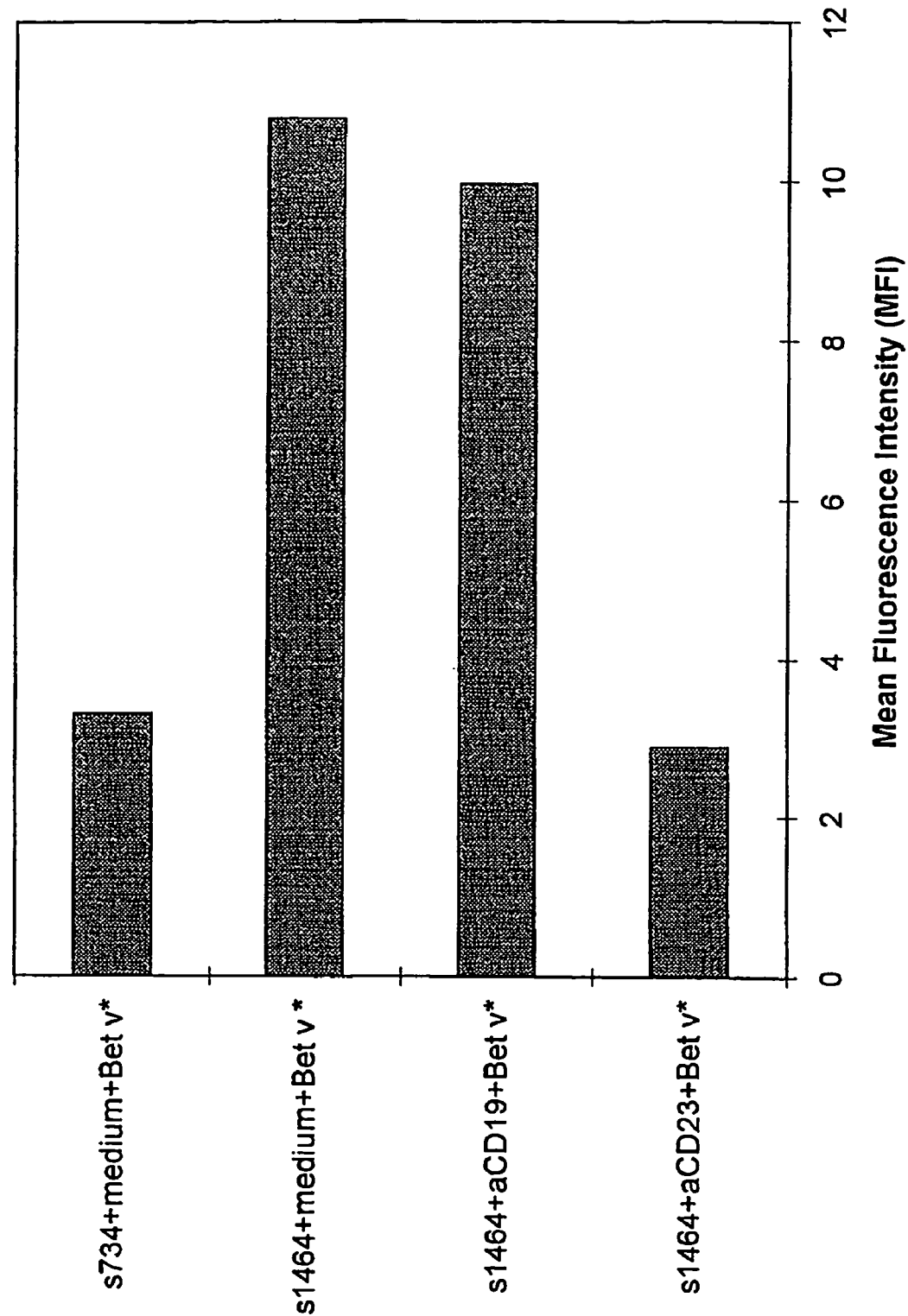
FIG. 1b shows the fluorescence level measured in an assay of the invention using (i) a control serum and allergen, (ii) allergic patient serum and allergen, (iii) allergic patient serum, antibody to CD19 and allergen, and (iv) allergic patient serum, antibody to CD23 and allergen.

In blocking experiments with antibody to CD23 and antibody to CD19 for reference, EBV-B cells were incubated for 1 hour at 4° C. with these antibodies before adding the cells to the mixtures of Bet v and serum. FIG. 1b shows the Mean Fluorescence Intensity (MFI) for (i) s734 serum, (ii) s1464, (iii) s1464 and antibody to CD19, and (iv) s1464 and antibody to CD23. As will appear from FIG. 1b the preincubation of the B cells with antibody to CD23 inhibits the binding of FITC-labelled birch extract to the B cells, whereas preincubation with an antibody to an irrelevant B cell surface antigen, CD19, does not inhibit the binding. This demonstrates that FITC-labelled birch extract binds to CD23, the low affinity IgE receptor.

Additional experiments, in which polyclonal anti-IgG or anti-IgE antibodies were preincubated with the allergic patient serum (s1464) for 1 hour at 37° C. before adding Bet v were carried out. FIG. 1c shows the Mean Fluorescence intensity (MFI) for (i) Background, (ii) s1464 and no Bet v, (iii) s1464 and Bet v, (iv) s1464, antibody to IgG and Bet v, (v) s1464, antibody to IgE and Bet v. As will appear from FIG. 1c IgE, but not IgG is responsible for the binding of FITC-labelled birch extract to the B lymphocytes.

In conclusion, the experiments shown in FIG. 1a-c show that the binding of a labelled allergen to CD23 on a solid carrier is mediated via IgE, and can easily be detected.

Example 2

The binding of birch allergen-specific IgE to CD23 is inhibited by immunotherapy sera even though cumulative birch allergen-specific IgE levels as measured by MagicLite® assay are increased.

FITC-labelled Betula verrucosa (Bet v) extract (1 µg/ml) was incubated with birch allergic patient serum 894 (>800 SU/ml birch-specific IgE in MagicLite® assay) at a final serum concentration of 40% in the absence or presence of a serum (also 40%) of a patient receiving birch SAV for >4 years (serum 1490, 88 SU/ml birch-specific IgE in MagicLite® assay). EBV transformed B cells from an allergic patient in culture medium were added to a final concentration of $4 > 10^6$/ml and incubated for 1 hour at 37° C., followed by two washes to remove excess allergen. After washing the cells, binding of FITC-labelled Bet v (Bet v*) to the B cells was analysed by measuring fluorescence using a FACSCalibur flowcytometer.

Figure 2A:
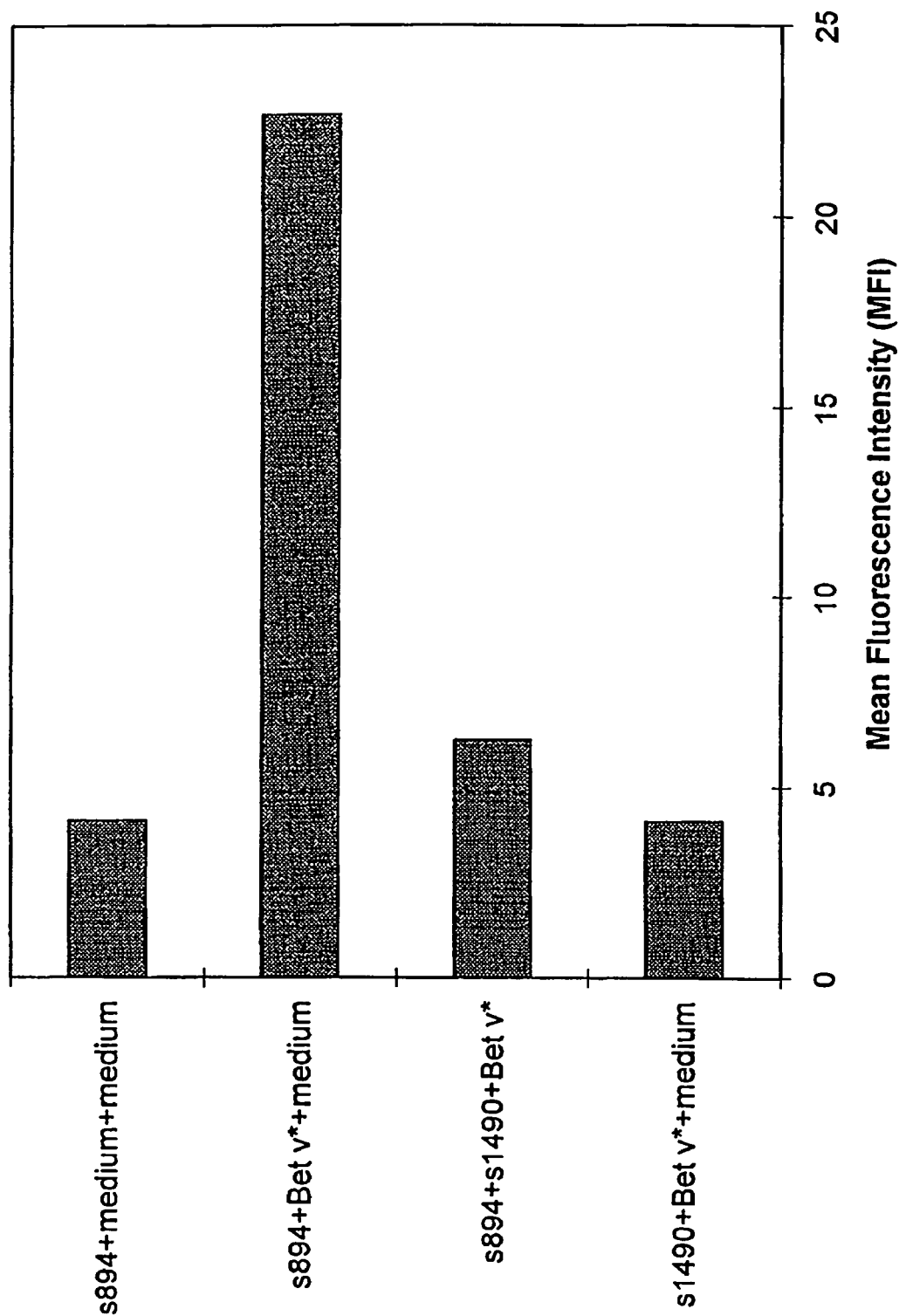
FIG. 2a shows the fluorescence level measured in an assay of the invention using (i) allergic patient serum and no allergen, (ii) allergic patient serum and allergen, (iii) allergic patient serum, SAV-treated allergic patient serum and allergen, and (iv) SAV-treated allergic patient serum and allergen.

FIG. 2a shows the Mean Fluorescence Intensity (MFI) for (i) s894 and no Bet v, (ii) s894 serum and Bet v, (iii) both s894 and s 1490 and Bet v, and (iv) s1490 and Bet v. As will appear from FIG. 2a the addition of s1490 reduces the binding of IgE and FITC-labelled birch allergen to CD23 to background levels. This indicates the presence of a factor that interferes with the IgE-mediated binding of FITC labelled birch allergen to CD23.

For comparison, FIG. 2b shows the calculated total level of birch allergen-specific IgE for the same reactant situations (i)-(iv) as in FIG. 2a, the levels being calculated on the basis of separate measurements of the total level of IgE in s894 and s1490 as measured by MagicLite® assay.

From FIG. 2a-b it may be concluded that the assay of the invention employing CD23 as capturing agent produces quite different results than the prior art total IgE assay MagicLite® employing antibody to IgE as capturing agent. Furthermore, it must be assumed that the results obtained by the assay of the invention better expresses the status of the subject examined, since in vivo antigen presentation is facilitated by CD23.

Example 3

Complexes between allergen and specific IgE bind to CD23 by interaction with the IgE-binding moiety of the receptor, and can be detected by an antibody to IgE.

Blocking experiments were carried out with three different monoclonal antibodies to CD23, viz. two antibodies to CD23 that bind specifically to the IgE binding moiety of CD23 (ML 233 from Pharmingen, sold by Becton-Dickinson, Denmark, and MHM6 from DAKO A/S, Denmark), and one antibody that binds specifically to a region of CD23 not involved in IgE binding (EBV CS5 from Becton-Dickinson, Denmark). Finally, an antibody to an irrelevant surface-molecule (CD14) was included as a reference (from DAKO A/S, Denmark). EBV transformed B cells were pre-incubated with 10 µg/ml of each antibody, for 1 hour at 4° C., washed to remove unbound antibody, prior to incubation with complexes. The complexes were generated by contacting serum s1464, from a donor with birch pollen allergy (>800 SU/ml birch-specific IgE in the Magiclite® assay) at a final serum-concentration of 80%, with 1 µg/ml Bet V, for 1 hour at 37° C. The complexes were allowed to contact the antibody-treated EBV-cells, for 1 hour at 4° C. Subsequently, the cells were washed, and bound complexes were stained by incubating with a biotinylated antibody recognising human IgE (PU PED0048 from ALK-Abello), followed by wash and incubation with a streptavidin-phycoerythrine conjugate (Southern Biotechnology Associates, sold by KEBO, Denmark). Following a final wash, binding of IgE-allergen complexes to the EBV cells was analysed by measuring fluorescence using a FACSCalibur flow cytometer.

From FIG. 6 it may be concluded that the binding of allergen to CD23 is mediated by interaction with the IgE-binding moiety of CD23, and not by a non-specific interaction. In addition, the binding of unlabelled complexes can easily be detected by an antibody to IgE.

Example 4

The invention allows for detection of specific IgE in sera from patients with allergy, irrespective of the allergen recognised.

Complexes were generated by contacting sera from two individual donors having allergy towards grass pollen (Phleuz p) allergens, (s1043: 582 SU/ml, and s1524: 65B SU/ml Phleam p-specific IgE in Magiclite® assay), with increasing doses of an extract of grass allergens. The reaction was allowed to proceed for 1 hour at 37° C. Subsequently, EBV transformed B cells were added to the reaction, for 1 hour at 4° C. The cells were washed, and bound complexes were visualised and analysed as described in Example 3. FIG. 7a shows the geometric mean of the fluorescence intensity for (i) s1043 and (ii) s1524. Each sample was run in duplicate, and the average was calculated.

In FIG. 7b, s1464 (described in Example 3) was contacted with increasing doses of purified, recombinant Bet v 1, one of the major allergens from Birch pollen. The experiment was performed as described for FIG. 7a.

FIGS. 7a and b show that in one embodiment of the invention, using the same antibody to IgE for detection, it is possible to measure IgE's specific for different allergens. The assay can be used for measuring IgE specific for whole allergen extract, as well as single, purified allergens. FIGS. 7a and b also demonstrate that individual allergens are required at different doses, in order to obtain an optimal signal.

Example 5

The binding of birch allergen-specific IgE to CD23 is inhibited by sera from patients who have undergone specific allergy vaccination (SAV) for birch-pollen allergy, whereas the binding is not inhibited by sera from a non-allergic donor, or a patient who have received SAV for an unrelated allergy.

Serum from a birch-pollen allergic donor, s1464, was mixed (1:1) with the following sera: (i) serum from a non-allergic donor s745 (0 SU/ml), (ii), (iii) donors who have received SAV for birch-pollen (s1490 and s1598; 88 and 57 SU/ml birch-specific IgE in Magiclite® assay, respectively), and (iv) donors with grass-pollen allergy (s808954; 137 SU/ml grass-specific, and 4 SU/ml birch-specific IgE in Magiclite® assay). Following incubation with either an extract of Birch-pollen allergens (Bet V, FIG. 8a), or a purified recombinant allergen from birch-pollen (Bet v 1, FIG. 8b), at a final concentration of 40% of each serum, EBV transformed B cells where added for one hour, at 4° C., the cells were washed, and bound complexes were detected as described above.

FIGS. 8a and b depicts the results as the geometric means of the fluorescence intensity. By comparing the total levels of IgE (measured in Magiclite® assays) in each sample (i-iv), to the signal obtained employing CD23 as a capturing agent, it can be concluded that the assay of the invention measures a different "type" of complex-forming, CD23-binding IgE. As explained above, the levels of this type, of IgE, is believed to better reflect the status of the subject examined than IgE-levels measured by conventional means.

LIST OF REFERENCES (1) "Serum-IgE-Facilitated Allergen Presentation in Atopic Disease", van der Heijden et al., The Journal of Immunology, Vol. 150, 3643-3650, 1993.
(2) "IgE-antigen complexes enhance FcεR and Ia expression by murine B lymphocytes", Richards et al., J. Exp. Med., Vol. 168, 571, 1998.
(3) Santamaria et al., Hum. Immunol., Vol. 37, 23-30, 1993.
(4) "The High Affinity IgE Receptor (FcεRI) Mediates IgE-Dependant Allergen Presentation", Maurer et al., The Journal of Immunology, Vol. 154, 6285-6290, 1995.

The invention claimed is:

1. A method of detecting and/or quantifying an IgE antibody specific to a ligand in the form of an antigen, an antibody, or a hapten in a liquid sample suspected to contain the IgE antibody comprising the steps of:
(a) contacting (i) the sample with (ii) a free dissolved ligand in the form of an antigen, an antibody, or a hapten to form a mixture I comprising complexes that comprise the IgE antibody and the ligand (IgE-containing complexes),
(b) mixing the mixture I with a carrier to which is bound (iii) an IgE receptor, wherein said IgE receptor is CD23 (FcεRII), to form a mixture II comprising carrier-bound IgE-containing complexes,
(c) separating the carrier-bound IgE-containing complexes from the mixture II, and
(d) determining the amount of the carrier-bound IgE-containing complexes formed by detecting a label present in the carrier-bound IgE-containing complexes,
wherein the label to be detected is associated with the ligand or the IgE antibody and wherein the label to be detected is added to the complexes present in steps (a), (b), or (c) and does not form part of the carrier.

2. The method according to claim 1, wherein the ligand is bound to biotin or a functional derivative thereof.

3. The method according to claim 1, wherein the IgE-containing sample is contacted with the ligand and allowed to incubate to form a mixture I (step (a)) before contacting mixture I with the carrier/IgE receptor (step (b)).

4. The method according to claim 1, wherein step (a) and (b) are carried out simultaneously in one operation.

5. The method according to claim 1, wherein the carrier is a particulate material.

6. The method according to claim 1, wherein the carrier is a paramagnetic particulate material.

7. The method according to claim 1, wherein the number of ligand molecules is between 100% and 200% of the number of IgE molecules to be detected.

8. A method of detecting and/or quantifying an IgE antibody specific to a ligand in the form of an antigen, an antibody, or a hapten in a liquid sample suspected to contain the IgE antibody comprising the steps of:
(a) contacting (i) the sample with (ii) a free dissolved labeled ligand in the form of an antigen, an antibody, or a hapten to form a mixture I comprising complexes that comprise the IgE antibody and the ligand (IgE-containing complexes),
(b) mixing the mixture I with a carrier to which is bound (iii) an IgE receptor, wherein said IgE receptor is CD23 (FcεRII), to form a mixture II comprising carrier-bound IgE-containing complexes,
(c) separating the carrier-bound IgE-containing complexes from the mixture II, and
(d) determining the amount of the carrier-bound IgE-containing complexes formed by detecting the label present in the carrier-bound IgE-containing complexes.

9. A method of detecting and/or quantifying an IgE antibody specific to a ligand in the form of an antigen, an antibody, or a hapten in a liquid sample suspected to contain the IgE antibody comprising the steps of:
(a) contacting (i) the sample with (ii) a free dissolved ligand in the form of an antigen, an antibody, or a hapten, wherein the ligand is bound to a label compound, to form a mixture I comprising complexes that comprise the IgE antibody and the ligand (IgE-containing complexes),
(b) mixing the mixture I with a carrier to which is bound (iii) an IgE receptor, wherein said IgE receptor is CD23 (FcεRII), to form a mixture II comprising carrier-bound IgE-containing complexes,
(c) separating the carrier-bound IgE-containing complexes from the mixture II, and
(d) determining the amount of the carrier-bound IgE-containing complexes formed by detecting the label present in the carrier-bound IgE-containing complexes.

10. A method of detecting and/or quantifying an IgE antibody specific to a ligand in the form of an antigen, an antibody, or a hapten in a liquid sample suspected to contain the IgE antibody comprising the steps of:
(a) contacting (i) the sample with (ii) a free dissolved ligand in the form of an antigen, an antibody, or a hapten and with (iii) a label compound to form a mixture I comprising complexes that comprise the IgE antibody and the ligand (IgE-containing complexes),
(b) mixing the mixture I with a carrier to which is bound (iv) an IgE receptor, wherein said IgE receptor is CD23 (FcεRII), to form a mixture II comprising carrier-bound IgE-containing complexes,
(c) separating the carrier-bound IgE-containing complexes from the mixture II, and
(d) determining the amount of the carrier-bound IgE-containing complexes formed by detecting the label present in the carrier-bound IgE-containing complexes,
wherein the label to be detected is associated with the ligand or the IgE antibody.

11. A method of detecting and/or quantifying an IgE antibody specific to a ligand in the form of an antigen, an antibody, or a hapten in a liquid sample suspected to contain the IgE antibody comprising the steps of:
(a) contacting (i) the sample with (ii) a free dissolved ligand in the form of an antigen, an antibody, or a hapten to form a mixture I comprising complexes that comprise the IgE antibody and the ligand (IgE-containing complexes),
(b) mixing the mixture I with a carrier to which is bound (iii) an IgE receptor, wherein said IgE receptor is CD23 (FcεRII), to form a mixture II comprising carrier-bound IgE-containing complexes,
(c) adding a label compound to the carrier-bound IgE-containing complexes formed in step (b),
(d) separating the carrier-bound IgE-containing complexes from the mixture II, and
(e) determining the amount of the carrier-bound IgE-containing complexes formed by detecting the label present in the carrier-bound IgE-containing complexes,
wherein the label to be detected is associated with the ligand or the IgE antibody.

12. A method of detecting and/or quantifying an IgE antibody specific to a ligand in the form of an antigen, an antibody, or a hapten in a liquid sample suspected to contain the IgE antibody comprising the steps of:
(a) contacting (i) the sample with (ii) a free dissolved ligand in the form of an antigen, an antibody, or a hapten to form a mixture I comprising complexes that comprise the IgE antibody and the ligand (IgE-containing complexes),
(b) mixing the mixture I with a carrier to which is bound (iii) an IgE receptor, wherein said IgE receptor is CD23 (FcεRII), to form a mixture II comprising carrier-bound IgE-containing complexes,
(c) separating the carrier-bound IgE-containing complexes from the mixture II,
(d) adding a label compound to the carrier-bound IgE-containing complexes resulting from the separation step (c) to form a mixture II',
(e) separating the labeled carrier-bound IgE-containing complexes from the mixture II', and
(f) determining the amount of the carrier-bound IgE-containing complexes formed by detecting the label present in the carrier-bound IgE-containing complexes,
wherein the label compound is associated with the ligand or the IgE antibody.

13. The method according to any one of claims 9-12, wherein the label compound is a chemiluminescent compound covalently bound to avidin, streptavidin, or a functional derivative thereof and the ligand is bound to biotin or a functional derivative thereof.

14. The method according to claim 13, wherein the chemiluminescent compound is an acridinium compound.

15. A method of evaluating the immunological status of a subject by detecting and/or quantifying an IgE antibody specific to a ligand in the form of an antigen, an antibody, or a hapten in a liquid sample suspected to contain the IgE antibody comprising the steps of:
   (a) obtaining a liquid sample suspected to contain an IgE antibody from the subject,
   (b) contacting (i) the sample with (ii) a free dissolved ligand in the form of an antigen, an antibody, or a hapten to form a mixture I comprising complexes that comprise the IgE antibody and the ligand (IgE-containing complexes),
   (c) mixing the mixture I with a carrier to which is bound (iii) an IgE receptor, wherein said IgE receptor is CD23 (FcεRII) and/or FcεRI, to form a mixture II comprising carrier-bound IgE-containing complexes,
   (d) separating the carrier-bound IgE-containing complexes from the mixture II, and
   (e) determining the amount of the carrier-bound IgE-containing complexes formed by detecting a label present in the carrier-bound IgE-containing complexes,
wherein the label to be detected is associated with the ligand or the IgE antibody, wherein the label to be detected is added to the complexes present in steps (b), (c) or (d) and does not form part of the carrier, and wherein the IgE to be detected is quantified using CD23 alone to obtain a first measurement and using FcεRI alone to obtain a second measurement, and using both the first and the second measurement as a basis for evaluating the immunological status of the subject.

16. A method of detecting and/or quantifying an IgE antibody specific to a ligand in the form of an antigen, an antibody, or a hapten in a liquid sample suspected to contain the IgE antibody comprising the steps of:
   (a) contacting (i) the sample with (ii) a free dissolved ligand in the form of an antigen, an antibody, or a hapten, to form a mixture I comprising complexes that comprise the IgE antibody and the ligand (IgE-containing complexes),
   (b) mixing the mixture I with a carrier to which is bound (iii) an IgE receptor, wherein said IgE receptor is CD23 (FcεRII), to form a mixture II comprising carrier-bound IgE-containing complexes,
   (c) separating the carrier-bound IgE-containing complexes from the mixture II,
   (d) adding a label compound coupled to an antibody to the IgE to be detected to the complexes present in steps (a), (b), or (c) above to form a mixture II',
   (e) separating the labeled carrier-bound IgE-containing complexes from the mixture II', and
   (f) determining the amount of the carrier-bound IgE-containing complexes formed by detecting the label present in the carrier-bound IgE-containing complexes.

17. The method according to claim 16, wherein the label compound is coupled to the antibody via biotin.

18. The method according to claim 16 or 17, wherein the label compound coupled to the antibody to the IgE to be detected is added to the carrier-bound complexes separated in step (c).

19. A method of detecting and/or quantifying a specific IgE antibody in a liquid sample suspected to contain the IgE antibody comprising the steps of:
   (a) contacting (i) the sample with (ii) a free ligand in the form of an antigen, an antibody, or a hapten to form a mixture I comprising complexes that comprise the IgE antibody and the ligand (IgE-containing complexes), wherein the ligand is bound to biotin or a functional derivative thereof,
   (b) mixing the mixture I with a carrier to which is bound (iii) an IgE receptor, wherein said IgE receptor is CD23 (FcεRII), to form a mixture II comprising carrier-bound IgE-containing complexes,
   (b') separating the carrier-bound IgE-containing complexes from the mixture II and washing said complexes,
   (b") adding to the washed carrier-bound IgE-containing complexes a solution of (iv) a chemiluminescent compound covalently bound to avidin, streptavidin, or a functional derivative thereof to form a mixture II',
   (c) separating the carrier-bound IgE-containing complexes from the mixture II' and washing the complexes, and
   (d) initiating a chemiluminescent reaction in the resulting IgE-containing complexes and detecting/measuring the resulting chemiluminescence, if any.

20. A method of monitoring and evaluating the immunological status of a subject comprising the steps of:
   (a) obtaining a liquid sample suspected to contain an IgE antibody from the subject,
   (b) contacting (i) the sample with (ii) a free ligand in the form of an antigen, an antibody, or a hapten to form a mixture I comprising complexes that comprise the IgE antibody and the ligand (IgE-containing complexes),
   (c) mixing the mixture I with a carrier to which is bound (iii) an IgE receptor, wherein said IgE receptor is CD23 (FcεRII), to form a mixture II comprising carrier-bound IgE-containing complexes,
   (d) separating the carrier-bound IgE-containing complexes from the mixture II, and
   (e) determining the amount of the carrier-bound IgE-containing complexes formed by detecting a label present in the carrier-bound IgE-containing complexes to obtain a measurement of the carrier-bound IgE-containing complexes,
wherein the label to be detected is associated with the ligand or the IgE antibody and wherein the label to be detected is added to the complexes present in steps (b), (c), or (d) and does not form part of the carrier, and wherein the measurement is used as a basis for monitoring and evaluating the immunological status of the subject.

21. A method of monitoring and evaluating the immunological status of a subject receiving Specific Allergy Vaccination (SAV) treatment comprising the steps of:
   (a) obtaining a liquid sample suspected to contain an IgE antibody from the subject,
   (b) contacting (i) the sample with (ii) a free ligand in the form of an antigen, an antibody, or a hapten to form a mixture I comprising complexes that comprise the IgE antibody and the ligand (IgE-containing complexes),
   (c) mixing the mixture I with a carrier to which is bound (iii) an IgE receptor, wherein said IgE receptor is CD23 (FcεRII), to form a mixture II comprising carrier-bound IgE-containing complexes,
   (d) separating the carrier-bound IgE-containing complexes from the mixture II, and
   (e) determining the amount of the carrier-bound IgE-containing complexes formed by detecting a label present in the carrier-bound IgE-containing complexes to obtain a measurement of the carrier-bound IgE-containing complexes,
wherein the label to be detected is associated with the ligand or the IgE antibody and wherein the label to be detected is added to the complexes present in steps (b), (c), or (d) and does not form part of the carrier, wherein the measurement is used as a basis for monitoring and evaluating the immunological status of the subject.

22. A method of detecting and/or quantifying physiologically active forms of an IgE antibody specific to a ligand in the form of an antigen, an antibody, or a hapten in a liquid sample suspected to contain the IgE antibody by simulating in vivo interactions between the IgE antibody, the IgE antibody's ligand and the IgE antibody's receptor, comprising the steps of:
   (a) contacting (i) the sample with (ii) a free dissolved ligand in the form of an antigen, an antibody, or a hapten to form a mixture I comprising complexes that comprise the IgE antibody and the ligand (IgE-containing complexes),
   (b) mixing the mixture I with a carrier to which is bound (iii) an IgE receptor, wherein said IgE receptor is CD23 (FcεRII), to form a mixture II comprising carrier-bound IgE-containing complexes, and wherein the complexes that comprise the IgE antibody and the ligand are formed prior to contact with the IgE receptor to simulate in vivo interactions between the IgE antibody, the ligand, and the IgE receptor,
   (c) separating the carrier-bound IgE-containing complexes from the mixture II, and
   (d) detecting and/or quantifying physiologically active forms of ligand-specific IgE bound to said receptor by determining the amount of the carrier-bound IgE-containing complexes formed by detecting a label present in the carrier-bound IgE-containing complexes,
wherein the label to be detected is associated with the ligand or the IgE antibody and wherein the label to be detected is added to the complexes present in steps (a), (b), or (c) and does not form part of the carrier and wherein in vivo interactions between the IgE antibody, the IgE antibody's ligand and the IgE antibody's receptor are simulated to measure physiologically active forms of the IgE antibody.

* * * * *